US00PP11324P

United States Patent [19]

Boeder

[11] Patent Number: Plant 11,324

[45] Date of Patent: Apr. 4, 2000

[54] CHRYSANTHEMUM PLANT NAMED 'CURLEW'

[75] Inventor: Mark Boeder, West Wittering, United Kingdom

[73] Assignee: Cleangro Limited, West Sussex, United Kingdom

[21] Appl. No.: 09/038,787

[22] Filed: Mar. 11, 1998

[51] Int. Cl.[7] ..... A01H 5/00

[52] U.S. Cl. ..... Plt./291

[58] Field of Search ..... Plt./287, 291, 288

*Primary Examiner*—Howard J. Locker

*Attorney, Agent, or Firm*—Christie, Parker & Hale, LLP

[57] ABSTRACT

A pot type Chrysanthemum plant with decorative light pink inflorescences which fade to near white with age.

2 Drawing Sheets

BACKGROUND OF THE INVENTION

The present invention is directed to a new and distinct variety of Chrysanthemum botanically classified as *Dendranthema grandiflora*. The varietal denomination of the new chrysanthemum is 'Curlew'.

The female parent of the new variety is an unnamed, undistributed seedling identified as 'G17-C4' and the male parent is an undistributed, unnamed, seedling identified as 'G3-C17'. The new variety has been asexually reproduced by vegetative cuttings in Ventura County, Calif. and the distinguishing characteristics are retained through successive generations of asexual reproduction.

SUMMARY OF THE INVENTION

'Curlew' is pot type Chrysanthemum plant with decorative light pink inflorescences which fade to near white with age.

BRIEF DESCRIPTION OF ILLUSTRATIONS

The accompanying photographs show a typical specimen of potted plant of the new variety and of flowers of the new variety, with colors being as nearly true as possible with illustrations of this type.

DESCRIPTION OF THE PLANT

Figure 1:
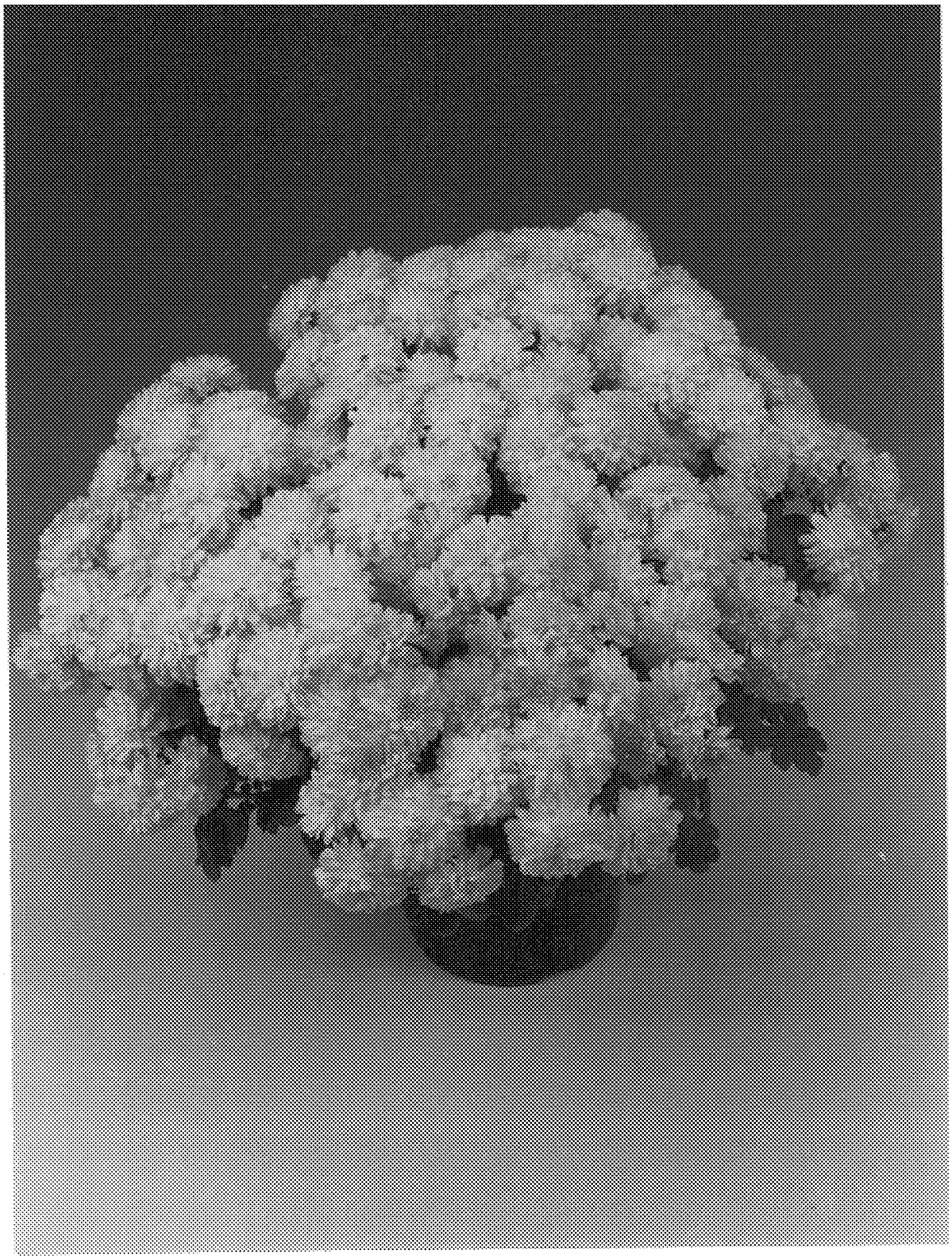
FIG. 1 is a whole plant view of the new cultivar grown in a pot.
Figure 2:
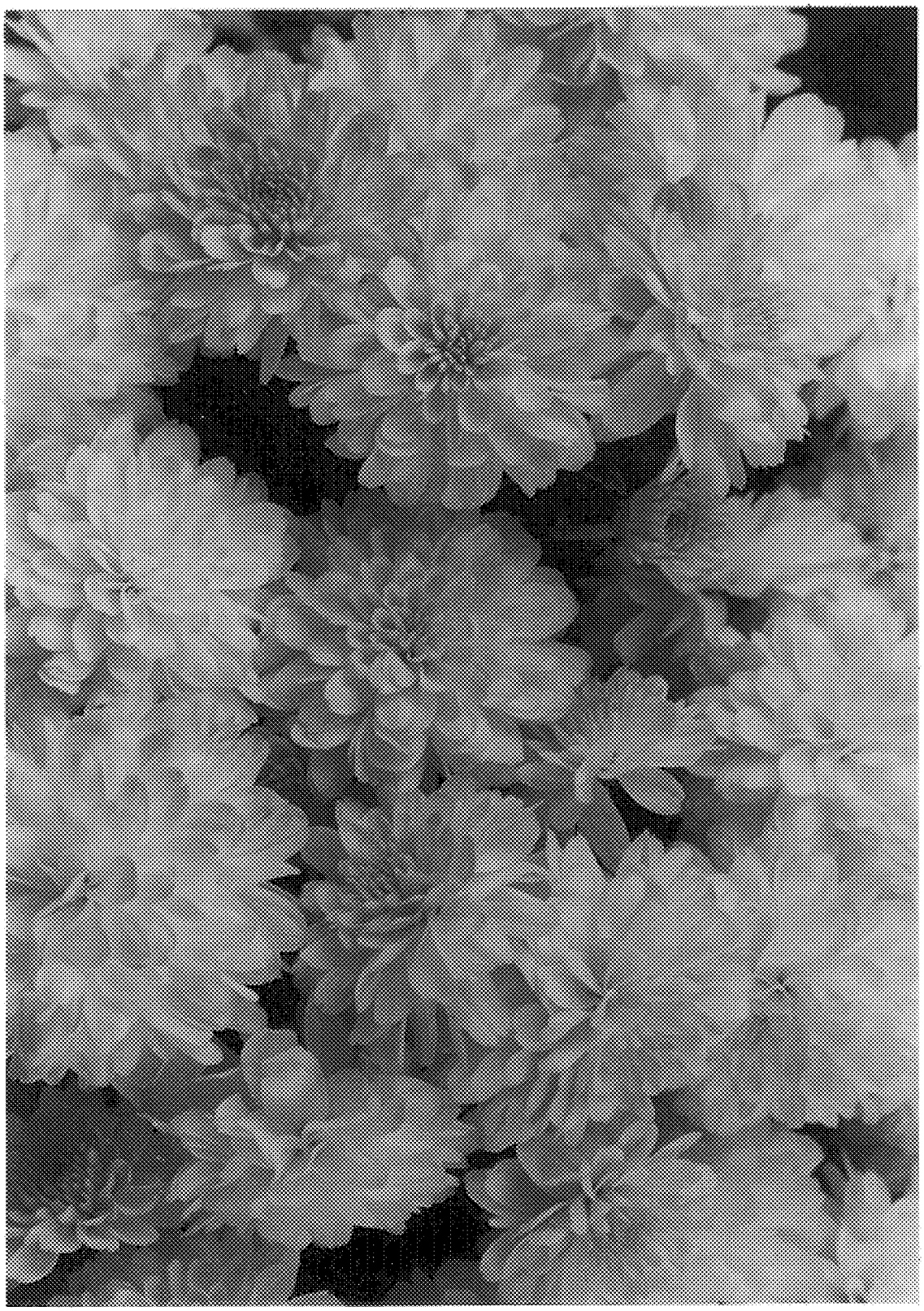
FIG. 2 is a closer view, showing inflorescence and foliage characteristics of the new cultivar in greater detail.

The following description of the new variety is of specimens grown in a greenhouse in Ventura County, Calif. in the month of October. 'Curlew' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once ten days after planting which results in about 4 breaks per pinch. It has been observed that the shelf life of 'Curlew' is about 27 days with the response time of about 7 weeks. No treatment with growth retardant is required. Useful growing conditions include night temperatures of about 64°–66° F., day temperatures of about 80°–85° F. and about 5,000 foot-candles of light.

Plant:

*Habit.*—Mounding.

*Height.*—About 22 cm.

*Number of breaks from pinch.*—About 4.

*Typical container sizes commercially grown in.*—4 inch, 6 inch, 1 and 3 gallon containers.

*Length of lateral branches.*—About 17 cm.

*Stem color.*—Near 146C.

Foliage:

*Leaf arrangement.*—Alternate.

*Number of leaves per lateral branch.*—About 17 fully expanded leaves.

*Leaf size.*—Length: About 6.2 cm. Width: About 3.8 cm.

*Leaf shape.*—Ovate.

*Attachment.*—Petioled.

*Leaf apex.*—Obtuse.

*Base.*—Tapered.

*Margin.*—Palmately lobed, slightly serrate.

*Aspect.*—Flat.

*Surface.*—Top: Pubescent. Bottom: Pubescent.

*Petiole length.*—About 1.5 cm. Color: Near 146D.

*Color.—Mature leaf: Top: Near* 137A. Bottom: Near 138A. Young leaf: Top: Near 137B. Bottom: Near 137C.

Flower:

*Inflorescence form.*—Cyme.

*Flower form.*—Decorative.

*Number of blooms per branch.*—About 15.

*Diameter of fully expanded bloom.*—About 4.5 cm.

*Depth of fully expanded bloom.*—About 2.5 cm.

*Sepal number.*—About 35. Color: Near 137B.

*General appearance of sepals.*—Thin, highly membranous margins.

*Peduncle.*—Length: Lower most peduncle is about 9 cm, terminal peduncle about 3.2 cm. Surface: Pubescent. Strength: Very sturdy.

*Flower bud shape.*—Spherical. Diameter: About 0.5 cm. Height: About 0.5 cm.

*Ray florets.*—Number per flower: About 170. Shape: Oblanceolate. Apex: 3 lobed. Base: Tapered. Margin: Entire. Aspect: Reflexed back, rolled inward at base. Length: About 2.1 cm. Width: About 0.8 cm.

*Disc florets.*—Number per flower: About 5. Shape: Tubular. Margin: Entire. Length: About 0.5 cm. Width: About 0.1 cm.

*Fragrance.*—slight.

Flower color:

*General flower coloration.*—Light pink throughout flower, slightly darker eye.

*Ray florets, top side.*—*Immature: Near* 62D. Mature: Near 62D. Fading: Near 155D.

*Ray floret, under side.*—Immature: Near 62D. Mature: Near 62D. Fading: Near 155D.

*Disc florets.*—Mature: Near 10A.

*Changes as the flower ages.*—Flower becomes lighter pink. Flower form becomes more rounded.

Reproductive organs:

*Ray florets.*—Pistillate. Stigma shape: 2 branched. Stigma color: Near 7A. Style length: About 0.5 cm.

*Disk florets.*—Stigma shape: Linear. Stigma color: Near 2C. Style Length: About 2 cm. Stamen number: About 5. Anther length: About 0.2 cm. Pollen color: Near 13A. Pollen quantity: Abundant.

What is claimed is:

1. A new and distinct Chrysanthemum plant of the variety substantially as herein shown and described.

* * * * *